(12) United States Patent
Atala (10) Patent No.: US 6,287,275 B1
(45) Date of Patent: Sep. 11, 2001

(54) SYSTEMS AND METHODS FOR PROMOTING TISSUE GROWTH

(75) Inventor: Anthony Atala, Weston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/228,018

(22) Filed: Jan. 11, 1999

Related U.S. Application Data (63) Continuation of application No. 08/326,711, filed on Oct. 20, 1994, now Pat. No. 5,858,003.

(51) Int. Cl.[7] .................................................. A61M 1/00
(52) U.S. Cl. ............................... 604/28; 604/31; 604/118; 604/175
(58) Field of Search ......................... 604/26, 514, 27–43, 604/118, 275, 500, 175; 128/898; 606/192

(56) References Cited

U.S. PATENT DOCUMENTS

| | | | |
|---|---|---|---|
| 3,477,438 | 11/1969 | Allen et al. | 128/349 |
| 3,720,199 | 3/1973 | Rishton et al. | 128/1 D |

(List continued on next page.)

FOREIGN PATENT DOCUMENTS

| | | |
|---|---|---|
| 0297723 | 1/1989 | (EP) . |
| 2290236 | 12/1995 | (GB) . |
| 8203557 | 10/1982 | (WO) . |
| 9213591 | 8/1992 | (WO) . |
| 9310723 | 6/1993 | (WO) . |
| 9612518 | 5/1996 | (WO) . |
| 9627406 | 9/1996 | (WO) . |
| 9850100 | 11/1998 | (WO) . |

OTHER PUBLICATIONS

Hu et al., "Full–Load Expansion Technique and Preliminary Clinical Application," *Plastic & Reconstructive Surgery*, Jun. 1994, vol. 93(7), pp. 1459–1464.

Keller et al., "Rapid Tissue Expansion for the Development of Rotational Skin Flaps in the Distal Portion of the Hindlimb of Dogs: An Experimental Study," *Veterinary Surgery*, Jan.–Feb. 1994, vol. 23(1), pp. 31–39.

Lailas et al., "Progressive Ureteral Dilation for Subsequent Ureterocystoplasty," *The Journal of Urology*, 1996, vol. 156, pp. 1151–1153.

Magovern et al., "A Permanent Arterial Access System," *ASIAO Transactions*, Jul.–Sep. 1988, pp. 460–462.

Seigert et al., "Epidermal Proliferation Rate After Skin Expansion in the Dog Model," *Laryngo–Rhino Otologie*, Apr. 1994, vol. 73(4), pp. 206–208 (In German with Abstract in English).

Spoonick et al., "Controlled Tissue Expansion in the Distal Extremities of Dogs," *Veterinary Surgery*, Nov.–Dec. 1993, vol. 22(6), pp. 436–443.

Wigness et al., "Bidirectional Implantable Vascular Access Modality," *ASAIO Transactions*, Apr. 14–16, 1982, pp. 54–57.

*Primary Examiner*—Mark Bockelman
(74) *Attorney, Agent, or Firm*—Thomas J. Engellenner; Nutter, McClennen & Fish, LLP (57) ABSTRACT

The present invention relates generally to the treatment of volume deficiency disorders of body structures and related syndromes, and more particularly to devices that deliver fluid at a controlled pressure into an interstice of a patient to effect tissue expansion and to surgical procedures for augmenting volumetrically deficient structures or for reconstructing damaged natural body tissue by attachment of tissue segments cultivated by dilation. Methods of delivering fluid at a controlled pressure into an interstice are also disclosed.

8 Claims, 4 Drawing Sheets

U.S. PATENT DOCUMENTS

| | | | |
|---|---|---|---|
| 3,875,939 | 4/1975 | Bolduc et al. | 128/235 |
| 4,237,935 | 12/1980 | Delmonte et al. | 137/860 |
| 4,258,721 * | 3/1981 | Parent et al. . | |
| 4,432,758 | 2/1984 | Finegold | 604/104 |
| 4,491,126 | 1/1985 | Cullor | 128/1 R |
| 4,585,435 | 4/1986 | Vaillancourt | 604/27 |
| 4,598,579 | 7/1986 | Cummings et al. | 73/37 |
| 4,681,564 | 7/1987 | Landreneau | 604/97 |
| 4,685,905 | 8/1987 | Jeanneret nee Aab | 604/247 |
| 4,701,160 | 10/1987 | Lindsay et al. | 604/53 |
| 4,834,705 | 5/1989 | Vaillancourt | 604/83 |
| 4,998,914 | 3/1991 | Wiest et al. | 604/67 |
| 5,049,132 | 9/1991 | Shaffer et al. | 604/101 |
| 5,084,015 | 1/1992 | Moriuchi | 604/96 |
| 5,092,846 | 3/1992 | Nishijima et al. | 604/165 |
| 5,112,303 | 5/1992 | Pudenz et al. | 604/49 |
| 5,122,122 | 6/1992 | Allgood | 604/174 |
| 5,176,662 | 1/1993 | Bartholomew et al. | 604/283 |
| 5,250,029 | 10/1993 | Lin et al. | 604/96 |
| 5,250,069 | 10/1993 | Nobuyoshi et al. | 606/192 |
| 5,279,583 | 1/1994 | Shober, Jr. et al. | 604/198 |
| 5,290,244 | 3/1994 | Moonka | 604/164 |
| 5,290,249 | 3/1994 | Foster et al. | 604/174 |
| 5,304,123 | 4/1994 | Atala et al. | 604/54 |
| 5,312,362 | 5/1994 | Pfolsgraf et al. | 604/167 |
| 5,334,170 | 8/1994 | Moroski | 604/80 |
| 5,437,629 * | 8/1995 | Goldrath . | |
| 5,459,700 | 10/1995 | Jacobs | 368/10 |
| 5,486,160 * | 1/1996 | Rossi et al. . | |
| 5,486,195 | 1/1996 | Myers et al. | 606/213 |
| 5,749,845 * | 5/1998 | Hildebrand et al. . | |
| 5,800,534 * | 9/1998 | Jeter et al. . | |
| 5,858,003 | 1/1999 | Atala | 604/175 |
| 5,984,943 * | 11/1999 | Young . | |

* cited by examiner

SYSTEMS AND METHODS FOR PROMOTING TISSUE GROWTH

This application is a continuation of application of Ser. No. 08/326,711 filed on Oct. 20, 1994, now U.S. Pat. No. 5,858,003 issued on Jan. 12, 1999.

BACKGROUND OF THE INVENTION

The present invention relates generally to the treatment of volume deficiency disorders and syndromes, and more particularly to devices that deliver fluid at a controlled pressure into an interstice of a patient to effect tissue expansion and growth of the surrounding tissue, and to surgical procedures for augmenting volumetrically deficient natural body structures or for reconstructing damaged natural body tissue by attachment of tissue segments cultivated by tissue expansion. Methods of delivering fluid at a controlled pressure into an interstice are also disclosed.

Biological volume deficiencies, such as short gut syndrome, are persistent conditions that result when the volumetric capacity of a natural body structure, such as a bladder or a lung, is insufficient to allow the organ to operate effectively or at all. Additionally, the lack of volumetric capacity can create internal fluid pressures and fluid refluxes that damage other organs and tissue. Among the many causes of such deficiencies are birth defects and abdominal trauma.

Presently, the afflicted population receives surgical treatment, typically in the form of augmentation procedures that increase volumetric capacity of the body structure by rebuilding the structure in a procedure that attaches a flap of additional tissue to the afflicted structure. For example, an infant born with insufficient bladder capacity can receive a bladder augmentation in a procedure that typically rebuilds the infant's bladder by attaching a flap of gastrointestinal tissue to the bladder wall. The surgeon attaches the gastrointestinal tissue to the bladder wall in a manner that increases the surface area of the surrounding wall and thereby increase the volumetric capacity of the bladder. Generally, the surgeon selects gastrointestinal tissue because this tissue normally is available in sufficient amounts within the patient to provide the needed tissue for the augmentation procedure Although these procedures are often quite successful at relieving the volumetric capacity deficiency of the body structure, the complications that arise from attaching different tissue types are often quite severe and persistent. For example, with respect to bladder augmentation by attachment of gastrointestinal tract, the resulting complications for any patient can include lithiasis, metabolic complications, increased mucous production, increased infections, perforations and even malignant growths within the treated body structure. It is generally understood by the medical community that these complications arise due to the attachment of a tissue type that lacks sufficient compatibility with the natural tissue of the body structure.

Therefore, an object of the present invention is to provide systems and methods for providing a supply of tissue that is more compatible with the augmentation or reconstruction procedure.

SUMMARY OF THE INVENTION

The present invention provides systems and methods for promoting the growth of biological tissue for use in surgical procedures that augment the volumetric capacity of an natural body structure or for use in reconstructive surgery. The present invention provides methods for promoting progressive tissue growth for use as additional integument in reconstructive procedures. To this end, the present invention discloses system and methods that introduce a pressurized fluid within a body structure, or an interstice of a patient. The pressurized fluid causes the surrounding tissue to expand and thereby creates a condition that is generally understood to promote tissue growth. The generated tissue can then be excised and employed during surgical augmentation procedures to relieve the condition of volume deficiency.

As used herein, the term "tissue expansion" is intended to encompass dilation of natural body lumens, stretching of tissue segments and promotion of "new tissue growth" in response to an applied pressure. The term "volume deficiency" is intended to encompass disorder and syndromes related to deficient volumetric capacity of a space or gap between tissue or within a natural body structure and includes by way of example, short gut syndrome.

Interstitial cavity, as the term is used herein, encompasses interstices in a tissue or structure of a natural body structure, spaces and gaps existing between layers of tissue or existing within organs, and can include interstices within the interior of the ureter, bladder, intestines, stomach, esophagus, trachea, lung, blood vessel or other organ, and will be further understood to include any surgically created interstice that defines an interior cavity surrounded by tissue.

In one aspect, the present invention encompasses devices for delivering fluids under pressure to an interstitial cavity within a patient. Generally, the devices include a catheter element that couples a source of fluid under pressure into fluid communication with the interstitial cavity, a valve element that is adapted to restrict the flow of the fluid to a select direction of flow and thereby prevent back flow of fluid, and an attachment element that forms a pressure resistant seal that couples the interstitial cavity into fluid communication with the catheter element.

In a preferred embodiment of the invention, the fluid delivering devices further include a pressure release element that reduces fluid pressure within the interstitial cavity by releasing fluid responsive to a user-selected fluid pressure limit. One realization of the pressure release element can be as a release port element that is arranged in fluid communication with the catheter element, and therefore, the fluid within the catheter, and that further includes a release plug that fluidity seals the release port to maintain fluid in the catheter as long as the fluid pressure is below a predefined threshold pressure and that is adapted to disengage from the release port responsive to the fluid in the catheter, or in the interstitial cavity, reaching the threshold fluid pressure limit.

The catheter element is adapted for conveying fluid under pressure to the interstitial cavity. The catheter element can include a silastic catheter tube that has a portion dimensionally adapted to fit within an interstitial lumen, such as the ureter. Depending upon the application, the catheter can be short or long section of silastic tube or other polymeric tubing that extends from a subcutaneous injection port and has the valve element incorporated therein. The interstitial cavity being dilated can be brought proximate to the catheter and coupled thereto by the attachment element.

The catheter element can further include a pointed tubular element adapted for penetrating tissue surrounding an interstitial cavity. The pointed element can attach to the distal end of the catheter and can be formed of a rigid material, such as poly methyl methacrylate, for penetrating tough fibrous membrane. The attachment element can be integrated with the catheter and can include a notched exterior surface for engaging the tissue surrounding the interstitial cavity and/or a threaded exterior surface adapted for rotationally engaging the tissue surrounding an interstitial cavity.

In one embodiment of the present invention, the fluid delivery system includes a catheter element that is surgically attached to an interstitial cavity and maintained as an intracorporeal catheter within the patient. The catheter connects to a port element that can include an injection port that has an elastic septum adapted for maintaining a fluid under pressure within the catheter element. The port can connect to a pump element that provides a source of fluid a selected pressure.

In another embodiment, the present invention can be realized as a fluid delivery system that includes a pump element for providing a source of fluid under pressure, a catheter element for conveying the fluid to the interior of the cavity, an injection port element that fluidity couples the pump element with the catheter element and a valve element that restricts the direction of fluid flow thereby preventing a back flow of pressurized fluid escaping through the injection port, and an attachment element that fluidity couples the catheter element to the interstitial cavity containing the fluid under pressure. The attachment element can couple to the tissue of the interstitial cavity to form a pressure resistant seal. A pressure resistant seal can include seals that can resist a fluid pressure applied against a joint of tissue.

In one embodiment, the pump element can comprise a syringe element that has a reservoir of fluid in fluid communication with a pressure sensor element, such as a manometer element, to indicate the pressure of fluid being introduced into the interstitial cavity. The hollow needle of the syringe element can penetrate the septum, and the septum can elastically form a pressure resistant fluid-tight seal around the penetrating needle. By action of the syringe piston, the fluid in the syringe reservoir is placed under sufficient pressure to introduce fluid into the catheter element and thereby into the interstitial cavity. The pressure sensor in fluid communication with the fluid reservoir responds to the pressure of the fluid introduced into the catheter and thereby provides a report of the fluid pressure introduced into the interstitial cavity. Thus, the pump element can be adapted to allow the selective control of the fluid pressure provided to the interstitial cavity.

In another embodiment, the pump element can include a motorized pump element, a fluid reservoir and a control element that includes a manometer or other pressure sensor in fluid communication with the fluid within the catheter element and a control circuit that responds to the measured fluid pressure to controllably operate the pump to maintain the proper fluid pressure within the interstitial cavity. In a further embodiment, the control element can include a processing unit that operates the motor pump to vary selectively over time the fluid pressure within the interstitial cavity. Preferably, the pump element has a mounting element for removably and replaceably mounting to the injection port element for selectively forming fluid communication with said catheter element.

The injection port element is adapted for fluidity coupling the pump element to the catheter element and can be integrally formed with the valve that is adapted to prevent pressurized fluid within the catheter from back flowing and escaping through the injection port element. The injection port can have a mounting element that is adapted for removably and replacably coupling in fluid communication to the pump element. The mounting element can be a threaded nipple, a latch or any other coupling that can form a pressure resistant fluid seal. In one embodiment, the injection port element can be an injection port that is adapted for subcutaneous implantation within a patient or for transcutaneous attachment to a patient.

The attachment element is adapted for placing the catheter element in fluid communication with the interstitial element and can form a pressure resistant seal between the catheter element and the interstitial cavity. As stated above, the attachment element can be integrated into the catheter element and can include a notched or barbed exterior surface located at a distal portion of the catheter element to engage the distal portion of the catheter with the tissue surrounding the interstitial cavity. Similarly, the distal end portion can have a threaded exterior surface that is adapted for rotationally engaging the tissue surrounding an interstitial cavity. The attachment means can further comprise a biocompatible, or natural, glue compound, such as a fibrin glue, and can comprise a mechanical attachment mechanism such as a cylindrical collar element, or an elastic o-ring, movably disposed on said catheter for slidingly engaging said catheter against the tissue wall surrounding the interstitial cavity.

In a further embodiment, the device can include a balloon element that connects in fluid communication to a distal portion of the catheter and that expands from a collapsed condition into an inflated condition responsive to fluid pressure. In the collapsed condition, the balloon can be dimensionally adapted for fitting within the interstitial cavity to be dilated, and in the inflated condition can be dimensionally adapted to volumetrically fill the interstitial cavity and thereby forcibly cause the tissue wall surrounding the cavity to stretch or expand. Additionally, the balloon element can be dimensionally adapted to extend into the intersitial cavity a select distance and thereby contact, in the inflated condition, only a portion of the interstitial cavity to promote tissue expansion in a select section of the surrounding tissue wall. Moreover, the balloon element can be adapted to contain the fluid and thereby prevent fluid from entering the interstitial cavity being dilated. Typically, the fluid is a saline solution, and preferably contains an antibacterial agent.

The device can additionally include a pressure release element that reduces fluid pressure by releasing fluid from within the cavity. The pressure release element can include a valve and pressure sensor disposed within the pump element, to measure the fluid pressure of the fluid provided to the catheter and to deactivate the pumping element in response to a fluid pressure within the catheter when the pressure exceeds a selected maximum pressure or to release fluid from within the catheter by action of the valve element.

In another aspect of the invention, methods are disclosed for treating volume deficiency disorders of body structures by augmenting a volumetrically deficient body structures. The methods employ a tissue dilation system that comprises a source of fluid under a select pressure, a catheter element for carrying said fluid under pressure to an interstitial cavity, a valve element for restricting said fluid under pressure to a select direction of fluid flow and an attachment element for forming a pressure resistant seal that couples said catheter element and an interstitial cavity into fluid communication. The method further includes the steps of preparing a portion of an interstitial cavity to receive a fluid under pressure, coupling the catheter element in fluid communication with the prepared portion of interstitial cavity and introducing fluid into the prepared portion to dilate a tissue wall of the interstitial cavity to cause tissue expansion and promote tissue growth. In a subsequent step, a portion of the dilated tissue wall is excised and attached to thee tissue wall of the volumetrically deficient body such that the volume capacity of the body is increased.

In a preferred practice, the method also includes the steps of monitoring the fluid pressure within the interstitial cavity; and releasing fluid from the interstitial cavity responsive to a select pressure level, to reduce the fluid pressure within the interstitial cavity.

In a further preferred practice of the invention, fluid under pressure is introduced into an interstitial cavity during select intervals, such as by daily introductions, to promote progressive tissue growth over a selected period of treatment. In one practice, saline fluid under pressure of approximately 5 to 15 mm can be introduced daily into an interstitial fluidity sealed cavity formed by clamping one section of a ureter to dilate the tissue wall of the ureter and thereby promote tissue expansion and growth thereof. The daily fluid introduction can be maintained for a period of thirty days or, more preferably, until the tissue wall has expanded sufficiently to provide a source of tissue for subsequent surgical augmentation or reconstructive procedure.

In one practice of the invention, the step of preparing a portion of an interstitial cavity includes selecting an interstitial cavity that has a wall of tissue phenotypically compatible with the volumetrically deficient cavity.

The term "phenotypically compatible tissue" as used herein, encompasses tissues that have similar tissue phenotype, similar gross cellular characteristics, can be similarly differentiated, histologically are similar, such as having compatible epithelial linings, or derived are from the same or similar embryonic structures.

In another aspect of the present invention, methods are provided for expanding tissue to promote tissue growth. The method includes the step of introducing fluid under a select pressure into an interstitial cavity by providing a pump element for providing fluid at a select pressure, fluidicly coupling a catheter element between the pump element and the interstitial cavity, providing a valve element within the catheter that prevents flow back by restricting the introduction of fluid to a select direction of fluid flow, and sealing fluid-wise the interstitial cavity to the catheter element.

DETAILED DESCRIPTION OF ILLUSTRATED EMBODIMENTS

The present invention provides systems and methods for expanding tissue promote the growth of biological tissue by introducing a pressurized fluid within an interstice of a patient.

To this end, the present invention encompasses fluid delivery systems that include a catheter element for coupling to a source of fluid under pressure and for delivering the fluid to the interior of an interstitial cavity, a valve element that restricts the direction of fluid flow thereby preventing back flow of pressurized fluid from escaping through the port, and an attachment element that fluidity couples the catheter element to the interstitial cavity containing the fluid under pressure.

Figure 1:
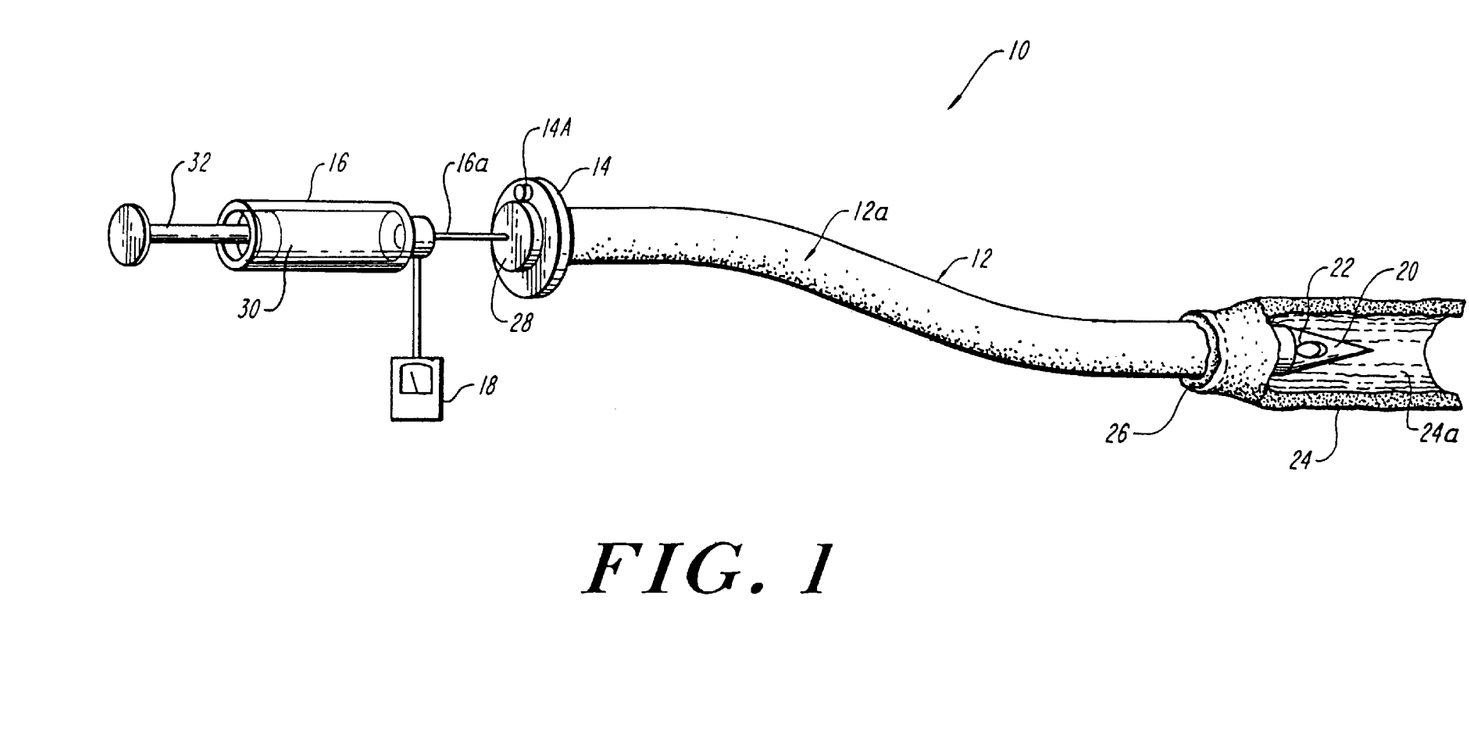
FIG. 1 illustrates one embodiment of the present invention for introducing fluid at a select pressure into an interstitial cavity.

FIG. 1 illustrates a system 10 constructed according to the present invention for delivering fluids at a select pressure into an interstitial cavity 24A. The system 10 includes a catheter element 12 that has a port element 14 with an optional safety release element 14A, a valve element 28, a pump element 16 having a manometer 18, a pointed distal end 20, an exit port 22 and an attachment element 26.

As illustrated in FIG. 1, the distal portion 20 of catheter element 12 is dimensionally adapted for fitting within the interstitial cavity 24A of a body structure 24. The fluid exit port 22 in the distal end 20 is in fluid communication with a hollow passage 12A that extends through the catheter element 22 that fluidity couples with the port element 14. The port element 14 in the illustrated embodiment includes an elastically deformable septum 28 that can be penetrated by a needle element 16A of the syringe pump element 16 illustrated in FIG. 1. The syringe pump element 16 illustrated includes a fluid reservoir 30 that contains a fluid, such as saline solution. Therefore, FIG. 1 illustrates a device that fluidity couples an interstitial cavity, such as the lumen 24A, to a reservoir 30 of fluid under pressure for delivering into the interstitial cavity fluid at a select pressure.

In the illustrated embodiment of FIG. 1, the catheter element 12 is a silastic catheter adapted for being subcutaneously inserted within a patient during the tissue expansion process. The catheter element 12 has a pointed distal end 20 that is adapted for penetrating natural body tissue. Preferably, the pointed distal end 20 is formed of a rigid biocompatible material such as poly methyl methacrylate (PMMA). An exit port 22 extends through the pointed end 20 to provide a fluid path into the interstitial cavity 24A. In the illustrated embodiment, the pointed distal end 20 of the catheter element 12 is dimensionally adapted for inserting into the lumen 24A of the natural body cavity the ureter. At the proximal end of the catheter element 12, the catheter is connected to a port element 14 that includes the valve element 28. Preferably, the catheter element 12 is coupled to the port element 14 in a pressure resistant fluid tight manner that maintains a seal between the catheter element 12 and the port element 14 when the catheter element 12 is filled with fluid under pressure. The distal end portion element 20 can be a separately manufactured element that couples to a catheter element 12 with a pressure resistant fluid tight seal that maintains a sealed connection between the catheter element 12 and the distal end element 20 when the catheter element 12 contains fluid under pressure. The catheter element 12 can be any of the silastic catheter elements that are sufficiently pressure resistant to contain fluid at the pressure level appropriate for the particular application.

The attachment element 26 illustrated in FIG. 1 is a layer of fibrin glue that forms a seal between the ureter wall 24 and the outer surface of the catheter element 12. The attachment element 26 provides a pressure resistant leak-proof seal between the catheter element 12 and the tissue that surrounds the interstitial cavity 24A.

In the illustrated embodiment, the system is used to promote tissue expansion of the ureter wall 24. In one practice of this application, the system 10 introduces fluids into the ureter lumen 24A at a pressure of between of 5–15 mm. The illustrated fibrin glue attachment element 26 is applied to the exterior surface of the catheter element in such quantities as to form a seal efficiently pressure resistant to maintain the catheter 12 within the lumen 24 when the lumen contains fluid under pressures of between 5–15 mm. Further, the catheter element 12 can be dimensionally adapted to frictionally engage the ureter wall 24. The quantity of fibrin glue, or any other natural glue appropriate to join the catheter element and tissue, is generally considered a determination within the skill of one of ordinary skill in the art of surgical procedures.

FIG. 1 further illustrates an optional safety release seal element 14A. The illustrated safety release element can be integrally formed with the port element 14, and includes a fluid channel (not shown) that connects the safety release seal to the fluid within the catheter 12. The illustrated seal element 14A has a plug element frictionally engaged within a port that couples in fluid communication with the integrally formed fluid channel. The plug element can be fitted into the port so that the plug disengages from the port when the fluid under pressure reaches a maximum pressure. The element plug; allows fluid to escape from the catheter, and therefore reduces pressure within the interstitial cavity 24A.

Figure 2A:
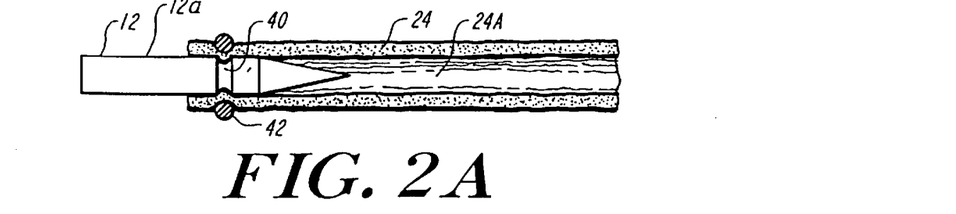
FIGS. 2A–2D illustrate certain embodiments of attachment elements that can be employed with the present invention to seal a catheter element to the tissue surrounding an interstitial cavity.

With reference to FIGS. 2A–2D, alternative structures for attachment means can 26 be described. FIG. 2A illustrates an attachment element that is integrally formed with the catheter element 12 as an exterior surface 12A that includes at least one notch 40 disposed about the periphery of the exterior surface 12A. The distal portion of the catheter element is inserted into the cavity 24 so that the notches 40 are disposed within the interior of the cavity 24A. An O-ring or similar clamping element 42, that is dimensionally adapted for fitting about the tissue wall 24, is fitted over the tissue wall at the point of the notches 40, to frictionally engage the tissue of the wall 24 within the notches 40. The O-ring 42 can be made of a biocompatible elastic material and can be dimensionally adapted to fit sufficiently tightly against the wall 24 to form a pressure resistant seal capable of resisting pressures necessary for their particular application, and, as a by-way of example, pressures of between 5 to 15 mm for introducing fluid into a ureter to cause tissue expansion and to promote tissue growth of the ureter wall.

Figure 2B:
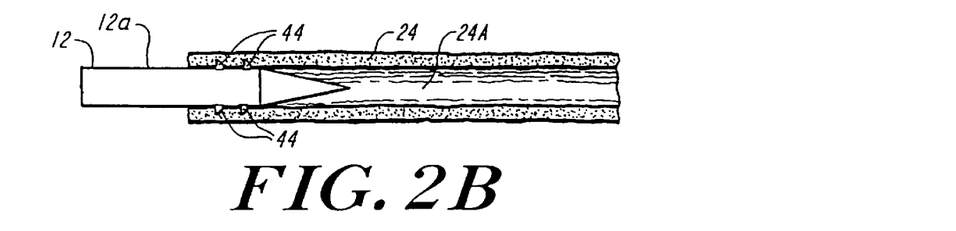

FIG. 2B illustrates a further alternative embodiment of the attachment element 26 that is integrally formed with the catheter 12 as barb elements 44 mounted along the exterior surface 12A of the catheter element 12. The illustrated barbs 44 engage the ureter wall 24 and are pitched proximally respective to the catheter element 12 to reduce movement of the catheter element 12 within the cavity 24A as pressurized fluid is introduced to the cavity 24A.

Figure 2C:
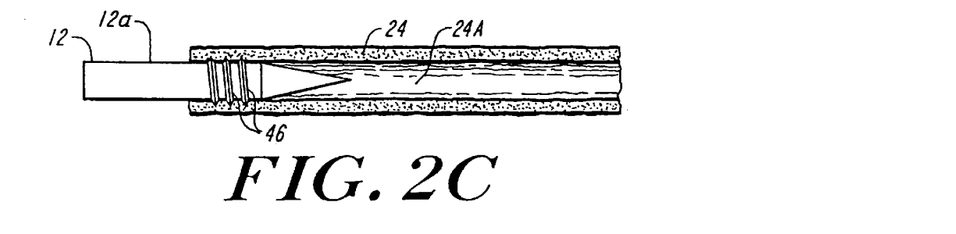

FIG. 2C illustrates yet a further embodiment of the attachment means 26 that includes a threaded exterior outer surface 12A that has threads 46 for rotatably engaging the wall 24 of the lumen 24A.

Figure 2D:
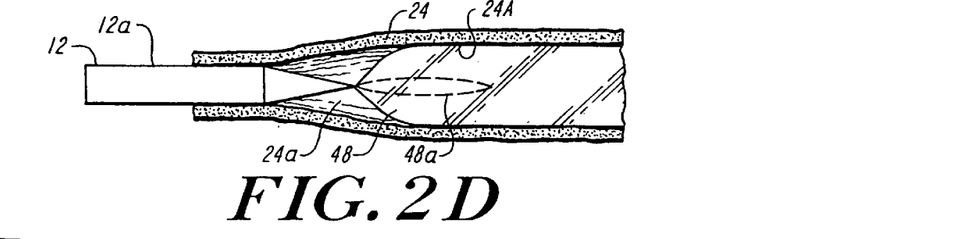

FIG. 2D illustrates yet another embodiment of the attachment means 26 that includes a balloon element 48 that has a first collapsed condition 48A, illustrated by the dotted lines in FIG. 2, and a second expanded condition 48. The balloon element of 48 connects in fluid communication to the catheter element 12 and expands responsive to fluid injected under pressure into balloon element 48. The outer exterior wall of the balloon element 48 frictionally engages against the wall of the interstitial cavity such as the wall 24. The balloon element 48 is dimensionally adapted so that in the expanded condition the balloon element 48 expands within the cavity 24A and expands the surrounding wall 24 in order to promote tissue growth. The fluid injected into the balloon element 48 is maintained within the balloon element during the tissue dilation procedure. This prevents the injected fluid from leaking into the interstitial cavity 24 and thereby provides a method for inflating certain body cavities that are not fluidity sealed or easily made fluidicly sealed by suturing or the like, such as lungs, trachea and blood vessels.

Referring again to FIG. 1, the port element 14 illustrated in FIG. 1 can be an injection port that has a valve 28 formed from a septum integrally constructed into the port element 14. The septum valve 28 can be an elastic membrane of the type commonly used in subcutaneously implanted injection ports and is a self-sealing membrane that forms a pressure resistant fluid seal around a needle element such as the hypodermic needle element 16A illustrated in FIG. 1 as penetrating the septum. By providing a septum valve 28 that seals about a needle element 16A with sufficient strength to prevent fluid contained under pressure within the catheter element 12 from escaping through the septum wall, the valve element 28 restricts fluid under pressure to a select direction of flow as it is introduced through the needle 16A into the catheter element 12, and thereby prevents flow back.

The pump element 16 illustrated in FIG. 1 is a syringe that has a needle element 16A adapted for carrying a fluid, a pressure sensor element 18, a fluid reservoir 30 and a piston element 32. The pressure sensor can be a manometer element 18 that couples in fluid communication to the fluid within the reservoir 30 and can indicate the pressure of the fluid within the reservoir 30 being injected into the catheter element 12. In operation, the piston element 32 is depressed into the fluid reservoir 30 to place the fluid under pressure and to inject the fluid through the hollow needle element 16A that has penetrated through the valve element 28. The septum valve 28 comprises a thickened portion of, preferably a silicone elastomer material having characteristics which permit repeated, intermittent puncture by a needle 16A for injecting fluid at a select pressure from the fluid reservoir 30. Such a needle 16A is preferably 20 gauge or smaller.

Figure 3:
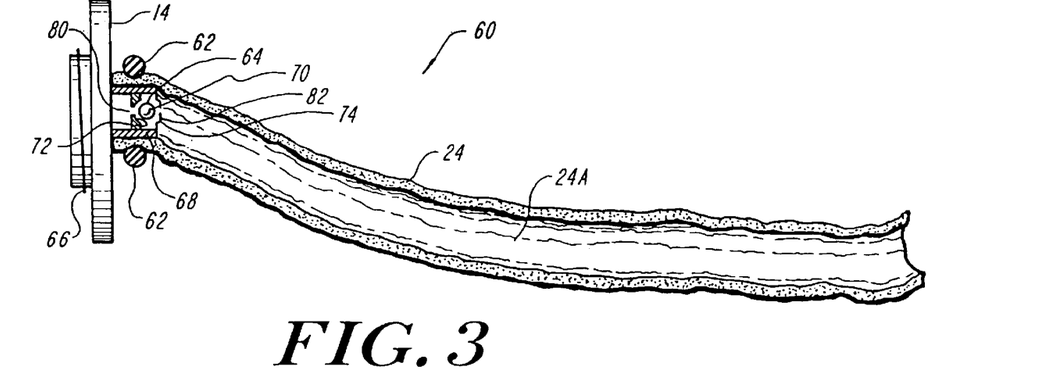
FIG. 3 illustrates in more detail one port element having a valve that restrict fluid flow to a select direction and a catheter element that extends as a nipple from the port element.

FIG. 3 illustrates a system 60 that represents an alternative embodiment of the present invention. System 60 includes the port element 14 an O-ring attachment element 62, a one-way valve element 64, a threaded coupling element 66 and a truncated catheter element 68. As illustrated in FIG. 1, an interstitial cavity 24A is fluidicly coupled to the valve element 64 for receiving fluid under pressure. The illustrated valve element 64 includes a ball element 70, a concave wall 72 that extends across the diameter of the truncated catheter element 68 and has a central aperture 80 disposed within the concave portion of the concave wall 72, and a distal wall 74 that includes plural apertures (not shown) as well as a displacement element 82 connected to the apertured distal wall 74 for maintaining the wall 70 at a position removed from at least one of the plural apertures.

In operation, a fluid source threadedly couples via the coupling element 66 to the port element 14. The pump element removably and replacably mounts to the port element 14 by threadingly engaging with the coupling element 66 to provide a pressure resistant, fluid tight seal between a pumping element and the device 60. Fluid at a select pressure is provided by the pumping element and introduced into the truncated catheter element 68 via port 14. The O-ring attachment element 62 forms a pressure resistant fluid tight seal between the wall of the interstitial cavity 24 and the catheter element 68. The O-ring 62, as discussed above, can be an elastically deformable, biocompatible ring dimensionally adapted for securing by frictional force the cavity wall 24 to a catheter element 62. As stated above, the one-way valve element 64 illustrated in FIG. 3 contains a ball element 70 that is displaceable within the valve 64. The fluid introduced under pressure to the catheter element 64 can pass through the aperture 80 and the proximally positioned apertured concave wall 72. The pressure of the fluid displaces the ball element 70 from the concave wall and the fluid travels through the one-way valve exiting the valve 64 via one or more of the plural apertures that extend through the distal wall 74. Once the source of fluid under pressure is decoupled from the port element 14, the fluid pressure within the interstitial cavity 24A acts on the ball element 70 to seat the ball element 70 within the apertured concave wall 72. The ball element 70 fluidicly seals the interstitial cavity 24A and thereby prevents the fluid under pressure from escaping through the catheter element 68 and port element 14.

The device 60 illustrated in FIG. 3, has a truncated catheter element 68 that can slidingly insert within the interstitial cavity 24A, that can be the ureter portion that remains unused after a transureteroureterostomy (hereinafter TUU) procedure.

The one-way valve element illustrated in FIG. 3, fluidicly seals the interstitial cavity 24A to thereby prevent a back flow of fluid from escaping from the cavity. The illustrated one-way valve 64 is merely one check valve that can maintain a closed condition responsive to fluid pressure in order to fluidicly seal a cavity element maintaining a fluid under pressure. It should be apparent to one of ordinary skill in the art that other one-way valves, check valves, and other pressure containment elements can be practiced with the present invention without departing from the scope thereof and it is considered to be within the skill of one of ordinary skill in the art to provide alternative one-way valve elements.

Figure 4:
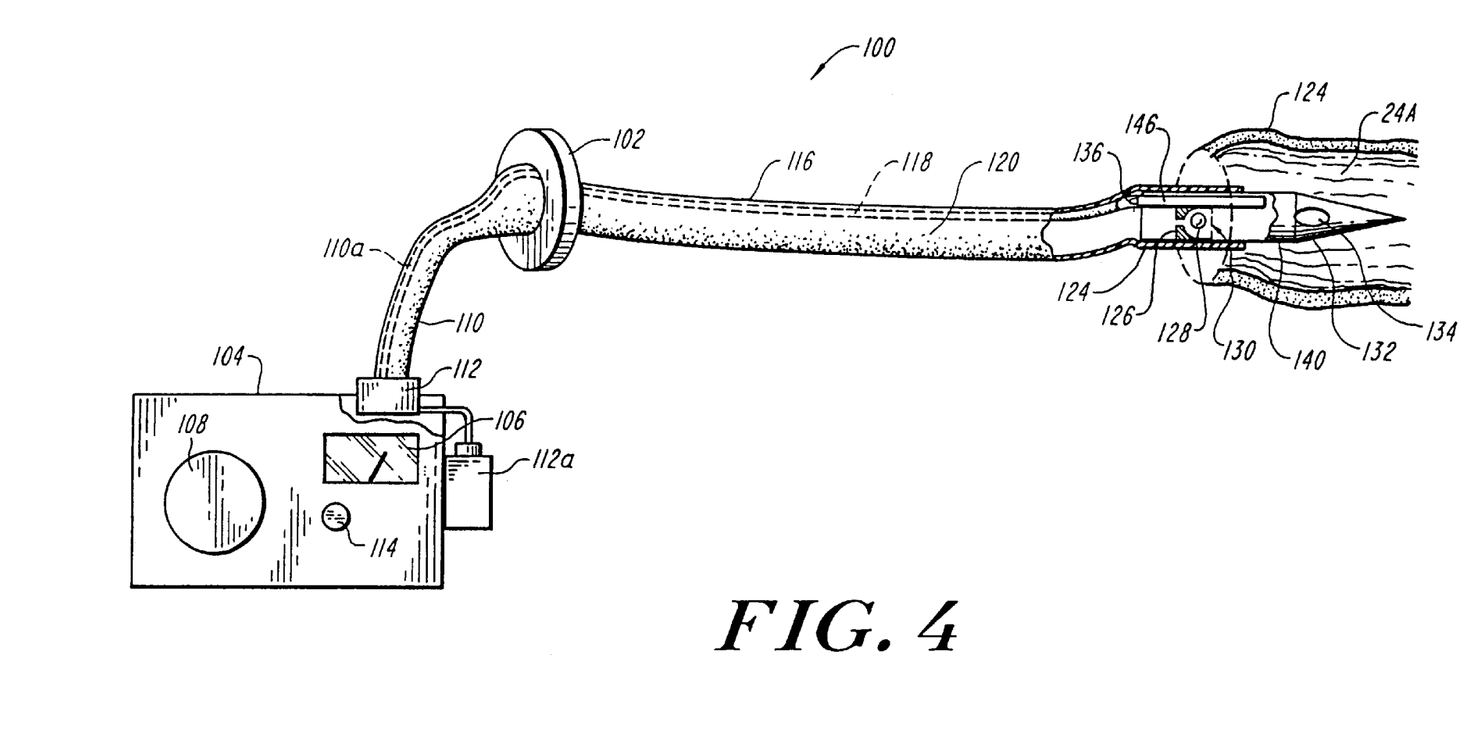
FIG. 4 illustrates an alternative embodiment of the present that invention includes a motorized pump element and a control element that operates the pump to selectively control the pressure of fluid introduced into the interstitial cavity.

FIG. 4 illustrates a system 100 that is a further alternative embodiment of the present invention for delivering and maintaining fluid under pressure within an interstitial cavity 24A. The system illustrated in FIG. 4 includes a pumping assembly 104, an injection port element 102, a catheter element 116, and a catheter assembly 140. The pumping assembly 104 illustrated in FIG. 4 includes a pressure indicator 106, a motor assembly 108, a connecting lumen 110 that includes, a feedback lumen 110A, a pressure release valve 112, a release reservoir 112A and pressure control knob 114.

The illustrated pumping element 104 can be any conventional fluid pumping element for providing a source of fluid under a select pressure. The pumping element 104 can be a peristaltic pump or any other conventional pumping system. The motor assembly 108 is an electric motor pump that moves fluid from a fluid reservoir (not shown) through the fluid delivery lumen 110, passed the injection port 102, through catheter 116 and into the interstitial cavity 24A. In one embodiment, the pressure indicator gauge 106 measures the pressure of fluid being pumped into the interstitial cavity 24A. The fluid pressure can be selectively controlled by an operator, by adjusting the control knob 114 that connects to a control element within the pump assembly 104 that controls the pumping motor 108 to establish a select fluid pressure for the fluid being pumped. The control element can include a manometer (not shown) that measures the fluid being forced through the lumen 110 and into the interstitial cavity 24A. The pump control element can be electrical circuit card assembly having a processing unit, data memory and program memory. The control element can operate in response to a program of processing unit instruction codes, to respond to the measured fluid pressure to maintain the selected pressure level, or to deactivate the pump if a maximum pressure limit is reached.

Alternatively, the illustrated pump assembly 104 can be employed with the illustrated catheter element 116 that includes a feedback lumen 118 that fluidicly couples the interstitial cavity 24A with a manometer (not shown) within the pump assembly 104. An operator selecting a pressure level via control knob 114 selects a pressure level in the interstitial cavity 24A to be achieved by the motor assembly 108. As illustrated in FIG. 4, the connecting lumen 110 includes a feedback lumen 110A that fluidicly couples to the feedback lumen 118A of the catheter element 116. A feedback lumen 110A can fluidicly connect to the manometer element within the pump assembly 104. Moreover, the feedback lumen 110A can connect to a pressure release element 112 within the pumping assembly 104.

The pressure release assembly 112 is in fluid communication with the feedback lumen 110A, and therefore in fluid communication with the fluid within the interstitial cavity 24A. The release valve 112 can be an electronically controlled release valve in an electrical circuit with the manometer element and control element pump, and adapted to that measures the fluid pressure. The release valve 112 can include an automated valve assembly that releases fluid into the release fluid reservoir 112A responsive to an operator selected threshold. In operation, the operator can select a threshold by adjusting the control knob 114 to achieve a selected level of fluid pressure within the interstitial cavity 24A. In a further embodiment of the present invention, the feedback lumen 118 can further connect to a safety release plug disposed on an exterior surface of the port element 102 to provide a safety release valve that releases fluid from the interstitial cavity 24A when the fluid pressure within the interstitial cavity 24A reaches a pressure that is sufficient to disengage a safety plug frictionally engaged within the safety release port. In one embodiment, the safety release port is disposed on an exterior surface of the port element 102 which is maintained exterior to the patient, so that fluid released from the interstitial cavity 24A does not release into the patients body cavity, nor is the pressure release plug prevented from disengaging from the release port due to tissue growth and blood clotting occurring on the safety port.

The catheter element 116 illustrated in FIG. 4 is adapted for providing the pump assembly 104 with a fluid feedback path. The fluid feedback lumen 118 illustrated in FIG. 4 provides fluid communication between the feedback lumen 110A and the fluid under pressure within the interstitial cavity 24A. As illustrated in FIG. 4, the catheter 116 has a distal portion that is dimensionally adapted to slide over a catheter assembly element 140 that can be fluidicly sealed about the periphery of the catheter assembly element 140 to the catheter 116 to provide a pressure resistance fluid tight seal between the catheter 116 and the catheter assembly 140.

As illustrated in FIG. 4, the catheter assembly 140 includes a feedback lumen 146 that has a connection nipple 136 at the proximal end which couples to the feedback lumen 118. The catheter assembly element 140 further includes the one-way valve element 126 that includes the ball element 128, a distal wall 130 and a proximal wall 124 having an aperture extending therethrough and having a concave shape. The catheter assembly element 140 further includes a pointed distal tip 132 that has an exit port 134 for releasing fluid into the interstitial cavity 24A.

The catheter assembly 140 can be attached by any of the attachment means previously described, to the wall 24 of the interstitial cavity 24A. The catheter assembly element 140 is removably and replacably coupled into fluid communication with the catheter element 116. The catheter assembly 140 can be dimensionally adapted for connecting into a selected natural body lumen, such as the ureter, and can have a proximal portion that is dimensionally adapted for connecting to a standard catheter element, such as the catheter 116. The catheter assembly element 140 is preferably made from a rigid biocompatible material such as PMMA to provide a rigid assembly, and a rigid pointed distal tip 132 that can penetrate through the tough fibers membrane of certain natural body lumens.

Figure 5A:
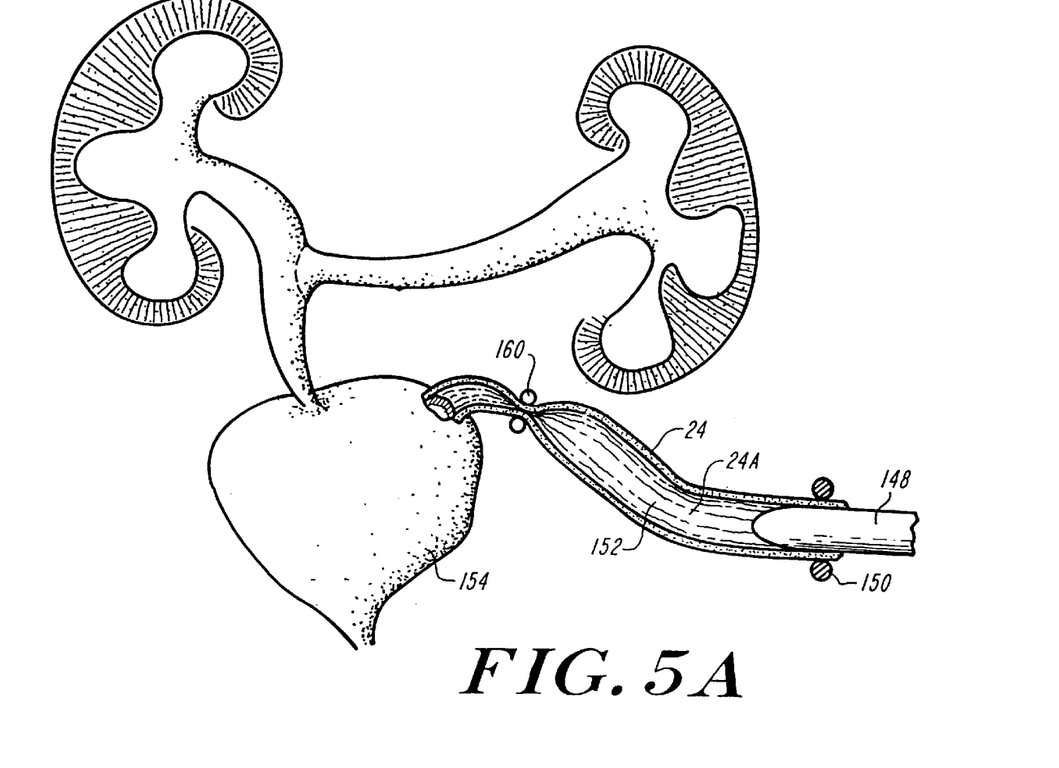
FIGS. 5A–5B illustrate a procedure for promoting tissue growth by introducing fluid under a select pressure into an interstitial cavity (the lumen of a ureter) and for augmenting the volumetric capacity of a bladder.
Figure 5B:
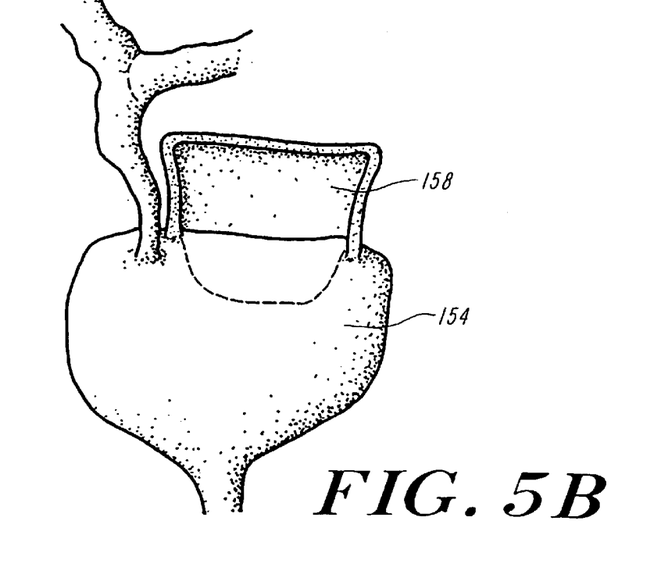

FIGS. 5A and 5B illustrate another aspect of the present invention that includes method for promoting progressive tissue growth for use in surgical procedures such as augmenting volumetrically deficient body structures and reconstructive surgery.

FIG. 5A illustrates the distal portion of a fluid delivery system 48 that is inserted within a interstitial cavity 24A that is depicted in Fig. 5A as the ureter. As further illustrated by FIG. 5, an attachment element 150 in the illustrated embodiment is an elastic O-ring, is slid which along the exterior surface of the tissue wall 24 to frictionally engage the tissue wall 24 against outer the exterior surface of the device 148. The O-ring attachment element 150 can form a pressure resistant fluid type seal that maintains the element 148 in fluid communication with the interstitial cavity 24A when the cavity contains fluid under pressure 152. As further illustrated by FIG. 5A, a clamping element 160 attached at a more distal section o f the tissue wall 24 to form a fluid seal at one section of the ureter. In this way, a chamber is formed within a natural body interstitial cavity that can contain a fluid under pressure 152. In practice, fluid is delivered through the element 148 into the cavity 24A at a select pressure, such as 5–15 mm. Preferably, the fluid is introduced into the cavity 24A in intervals in order to progressively promote tissue growth. As the wall 24 of the interstitial cavity 24A expands due to the force of pressure against the wall, the fluid pressure diminishes within the cavity 24A. At subsequent intervals, more fluid can be introduced into the cavity element 24A. Alternatively, one in practice of the invention, the device 148 continuously delivers fluid into the chamber 24A each time fluid pressure is detected far below a selected pressure level.

Once the tissue wall 24 has expanded sufficiently, a portion, or the entire wall, is excised in a surgical procedure. Typically the clamping element 160 is replaced by a permanent stitch and the wall 24 is made available for subsequent surgical procedures such as augmentation or surgical reconstruction.

FIG. 5B illustrates a tissue flap 158 that comprises the tissue wall 24 illustrated in FIG. 5A that has been expanded to a size appropriate for successfully augmenting the bladder 154. In a surgical bladder augmentation procedure, the tissue flap 150A is added to the bladder 154 in a manner that increases the surface area of the bladder and thereby increases the volume metric capacity of the bladder.

The invention will next be described in connection with a non-limiting experimental protocol.

The complications associated with bladder augmentation using the gastrointestinal tract are well known. These include malignancy, lithiasis, metabolic complications, increased mucus production, increased infections, and perforation. We have designed a system wherein progressive dilation can be performed in a normal ureter which can be subsequently used for augmentation.

Ten rabbits underwent unilateral ureteral ligation at the ureterovesical junction and ipsilateral nephrectomy. A silastic catheter was threaded into the proximal ipsilateral ureter and connected to a device for introducing fluid under pressure to an interstitial cavity. The device included an injection port that was secured subcutaneously. Fibrin glue was used as an additional sealant. Ten days to two weeks after surgery, a saline-antibiotic solution was injected daily subcutaneously into the palpable injection port. Baseline cystography and cystometrograms were performed with an accurate measurement of bladder capacity. Ureterography was performed initially and then weekly by injecting contrast media in the ureter. Within 30 days, the ureteral units were dilated at least 10 fold, as measured by radiography. A second procedure was performed in each animal. The dilated ureteral diameter exceeded that of adjacent colon in each instance. Augmentation cystoplasty was performed with the reconfigured dilated ureteral segment. Repeat cystography and cystometrograms showed an increased bladder capacity ranging from 190% to 380% (average 260%).

This system of progressive ureteral dilation could be easily applied to the clinical setting. Patients who previously had, or are having a nephrectomy or transureteroureterostomy (TUU), with an unused ureteral segment, would be ideal candidates for this approach. In addition, patients with normal diameter ureters, requiring bladder augmentation, could undergo a TUU and connection of the injection port to the unused ureteral portion. Within 6 weeks after periodic ureteral dilation, the patient could return for bladder augmentation through a simple lower abdominal incision.

This system can also be used to dilate and expand growth of tissues in other organ systems where tissue shortage is present. Patients with a short gut syndrome who are born with or acquire a limited amount of gastrointestinal tract, would also be ideal candidates for this technology. Currently, some patients with the short gut syndrome have no therapeutic recourse and die. The system of tissue dilation and expansion could also be used for patients with inadequate lung volume either due to congenital or acquired conditions. These patients usually require extracoporeal membrane oxygenation (ECMO), which in of itself, carries an 80% mortality rate. Hydraulic tissue expansion could be performed through the trachea with a similar device into an individual lung organ while the patient is on ECMO. This system could also be utilized to expand individual blood vessels which could later be used for any type of vascular bypass surgery as graft material, such as that needed in aorto-femoral surgery, thereby avoiding the need for artificial materials such as polytetrafluoroethylene (Teflon) grafts, which are associated with various complications. This system could also be used for local tissue expansion, such as for skin or scalp areas where additional integument is needed for reconstructive purposes. This system could be further used for bladder augmentation, urethral dilation, ureteropelvic junction obstruction repair, ureterovesical junction obstruction repair or any area at in the body where an obstructive process occurs due to strictures, adynamic segments, or lack of tissue. This system could also be for gastric dilation, expansion of tracheal tissue, esophageal enlargement, intestinal expansion, and any area at where dilation or tissue expansion is required.

The present invention has been described with reference to certain illustrated embodiments. However, those skilled in the art will recognize, or be able to ascertain using no more than routine experimentation, many equivalents to the specific embodiments of the invention described herein. The invention and such equivalents are to be understood and determined by reference to the following claims.

I claim:

1. A method of expanding an interstitial cavity of a body structure to promote tissue growth and volumetric augmentation of the body structure, comprising the steps of:

provided a tissue dilation system comprising a source of fluid, a catheter element for carrying fluid to an interstitial cavity of the body structure, a valve element for restricting back flow of fluid and an attachment element for forming a pressure resistant seal that couples the catheter element and the interstitial cavity into fluid communication;

coupling the tissue dilation system to the interstitial cavity; and introducing fluid under pressure into the interstitial cavity such that at least some of the fluid contacts the body structure and dilates a tissue wall of the interstitial cavity for a period of time such that tissue growth and volumetric augmentation occur, and such that the body structure retains an increased volumetric capacity after removal of the fluid from the body.

2. The method of claim 1, further comprising the steps of:

monitoring the fluid pressure within the interstitial cavity, and releasing fluid from the interstitial cavity responsive to a select pressure level to reduce the fluid pressure therein.

3. The method of claim 1 wherein the step of introducing said fluid under pressure into the interstitial cavity further comprises:

introducing the fluid through the use of a pump element.

4. The method of claim 1, wherein the interstitial cavity is a ureter.

5. The method of claim 4, wherein fluid is introduced into the ureter at a pressure of between about 5 mm to about 15 mm.

6. The method of claim 1, wherein the interstitial cavity is a bladder.

7. The method of claim 6, wherein fluid is introduced into the bladder at a pressure of between about 5 mm to about 15 mm.

8. A method of expanding a ureter to promote tissue growth, comprising the steps of:

providing a tissue dilation system comprising a source of fluid, a catheter element for carrying fluid to the ureter, a valve element for restricting back flow of fluid and an attachment element for forming a pressure resistant seal that couples the catheter element and the ureter into fluid communication;

preparing the ureter by clamping a section of the ureter to form a fluid containing chamber within the ureter;

coupling the tissue dilation system to the ureter; and introducing fluid under pressure into the ureter to dilate a tissue wall of the ureter and thereby promote tissue expansion.

* * * * *